US010532964B2

(12) United States Patent
Kalluru et al.

(10) Patent No.: US 10,532,964 B2
(45) Date of Patent: Jan. 14, 2020

(54) REAGENT PURIFICATION SYSTEMS, METHODS, AND APPARATUS

(71) Applicant: Iowa State University Research Foundation, Inc., Ames, IA (US)

(72) Inventors: Sri Harsha Kalluru, Ames, IA (US); Nacu Hernandez, Ames, IA (US); Eric W. Cochran, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 6 days.

(21) Appl. No.: 15/593,804

(22) Filed: May 12, 2017

(65) Prior Publication Data

US 2017/0327438 A1 Nov. 16, 2017

Related U.S. Application Data

(60) Provisional application No. 62/335,782, filed on May 13, 2016.

(51) Int. Cl.
| | |
|---|---|
| *C07C 7/12* | (2006.01) |
| *B01D 15/34* | (2006.01) |
| *B01D 15/36* | (2006.01) |
| *B01J 20/08* | (2006.01) |
| *B01J 20/10* | (2006.01) |

(Continued)

(52) U.S. Cl.
CPC ............. *C07C 7/12* (2013.01); *B01D 15/34* (2013.01); *B01D 15/361* (2013.01); *B01J 20/08* (2013.01); *B01J 20/103* (2013.01); *B01J 20/281* (2013.01); *B01J 47/02* (2013.01); *B01J 2220/52* (2013.01)

(58) Field of Classification Search
None
See application file for complete search history.

(56) References Cited

U.S. PATENT DOCUMENTS

2012/0046512 A1* 2/2012 Gauthier ............... B01J 23/755
585/841

FOREIGN PATENT DOCUMENTS

GB 1030451 * 5/1966

OTHER PUBLICATIONS

Lee, Hyung-Woo, et al., "Mini-Pilot Scale Production of Homopolymer and Block Copolymer by Anionic Polymerization," J. Ind. Eng. Chem., vol. 7, No. 4 (2001) pp. 204-211.

(Continued)

*Primary Examiner* — Tam M Nguyen
(74) *Attorney, Agent, or Firm* — McKee, Voorhees & Sease, PLC (57) ABSTRACT

Herein disclosed is an economical standalone system that replaces conventional monomer purification methods needed to perform chemical reactions that require reactants with a high degree of purity. Chemical reactions, such as anionic polymerization, can produce highly monodisperse homopolymers and block copolymers, however to do so they require very high purity reactants along with a moisture and oxygen free atmosphere. The system and method uses traditional column purification methods, but incorporates them into an economical, standalone, compact, and hazard free system. This method is different in view of safety, cost of cleaning procedure, time commitment, space availability, design and operational ease; helping researchers save time by cutting down the operating commitment by 90% and most importantly making it safer.

16 Claims, 7 Drawing Sheets

(51) Int. Cl.
*B01J 20/281* (2006.01)
*B01J 47/02* (2017.01)

(56) References Cited

OTHER PUBLICATIONS

Pangborn, Amy B., "Safe and Convenient Procedure for Solvent Purification," Organometallics 1996, 15, pp. 1518-1520.
Mitch, "Tert-Butyllithium Claims Fellow Chemist at UCLA" Jan. 20, 2008, http://www.chemistry-blog.com/2009/01/20/tert-butyllithium-claims-fellow-chemist-at-ucla/.

* cited by examiner

REAGENT PURIFICATION SYSTEMS, METHODS, AND APPARATUS

CROSS-REFERENCE TO RELATED APPLICATIONS

This application claims priority under 35 U.S.C. § 119 to provisional application Ser. No. 62/335,782, filed May 13, 2016, which is herein incorporated by reference in its entirety.

FIELD OF THE INVENTION

The disclosure relates generally to monomer purification needed to perform chemical reactions. More particularly, but not exclusively, the disclosure relates to a standalone system for purifying reactants with a high degree of purity.

BACKGROUND OF THE INVENTION

In conventional purification methods, monomers and/or other reactive chemicals are reacted with highly oxidative reagents, i.e. alkyl lithium or alkyl magnesium, forming insoluble salts with the inhibitors and impurities. The monomers are then distilled off and the process is repeated several times until the desired purity is achieved. The use of alkyl lithium or alkyl magnesium, labeled as "highly flammable", can catch fire spontaneously if exposed to air, can be fatal if swallowed, can cause severe skin burns and eye damage, may cause drowsiness or dizziness, can be very toxic to aquatic life with long lasting effects, and has caused many lab accidents (from minor burns to even deaths) when exposed to air, water, or other protic chemicals. Additionally, conventional cleaning procedures require experienced personal to get best results.

Therefore, there is a need in the art for a monomer purification system, method, and/or apparatus that purifies monomers and other reagents with a high degree of purity with improved safety, shortened time, and being economical.

SUMMARY OF THE INVENTION

It is therefore a primary object, feature, and/or advantage of the present disclosure to improve over the state of the art.

It is another object, feature, and/or advantage of the disclosure to provide an economical and safe system, method, or apparatus for purifying monomers and other reagents.

It is still another object, feature, and/or advantage of the disclosure to provide a purification system that can be portable.

It is yet another object, feature, and/or advantage of the disclosure to provide a purification system that purifies reagents in a shortened time.

It is a further object, feature, and/or advantage of the disclosure to that can be used to purify a broad range of reactive chemicals.

It is still a further object, feature, and/or advantage of the disclosure to provide a system that does not require dedicated training.

These and/or other objects, features, and advantages of the disclosure will be apparent to those skilled in the art. The disclosure is not to be limited to or by these objects, features and advantages. No single embodiment need provide each and every object, feature, or advantage.

The present disclosure presents an economical, standalone system that replaces conventional monomer (and other reactive chemical) purification methods needed to perform chemical reactions (e.g. anionic polymerizations, RAFT polymerizations, ATRP, ROMP) that require reactants with a high degree of purity. Chemical reactions, such as anionic polymerization, can produce highly monodisperse homopolymers and block copolymers, however, to do so they require very high purity reactants along with a moisture, oxygen, and protic free environment.

The approach uses traditional column purification methods used by industry, but incorporates them into an economical, standalone, compact, and hazard free system. This method is different in view of safety, cost of cleaning procedure, time commitment, space availability, design and operational ease; helping researchers save time by cutting down the operating commitment by 90% and most importantly making it safer. The disclosure also eliminates the concern of dedicating a large amount of lab space for the purification system, giving the user option of collecting the purified monomer air free; all at a very economical and facile way.

The system according to aspects of the disclosure allows for replacing components (e.g., columns) in an easier and user friendly manner, while reducing the time needed and minimizing the exposure of the components of the system to outside atmosphere. Still further, the disclosure provides for apparatus, systems, and/or methods for refilling the chemical holding reservoir in a way that improves upon what is currently offered.

Various embodiments of the invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENTS

Figure 1:
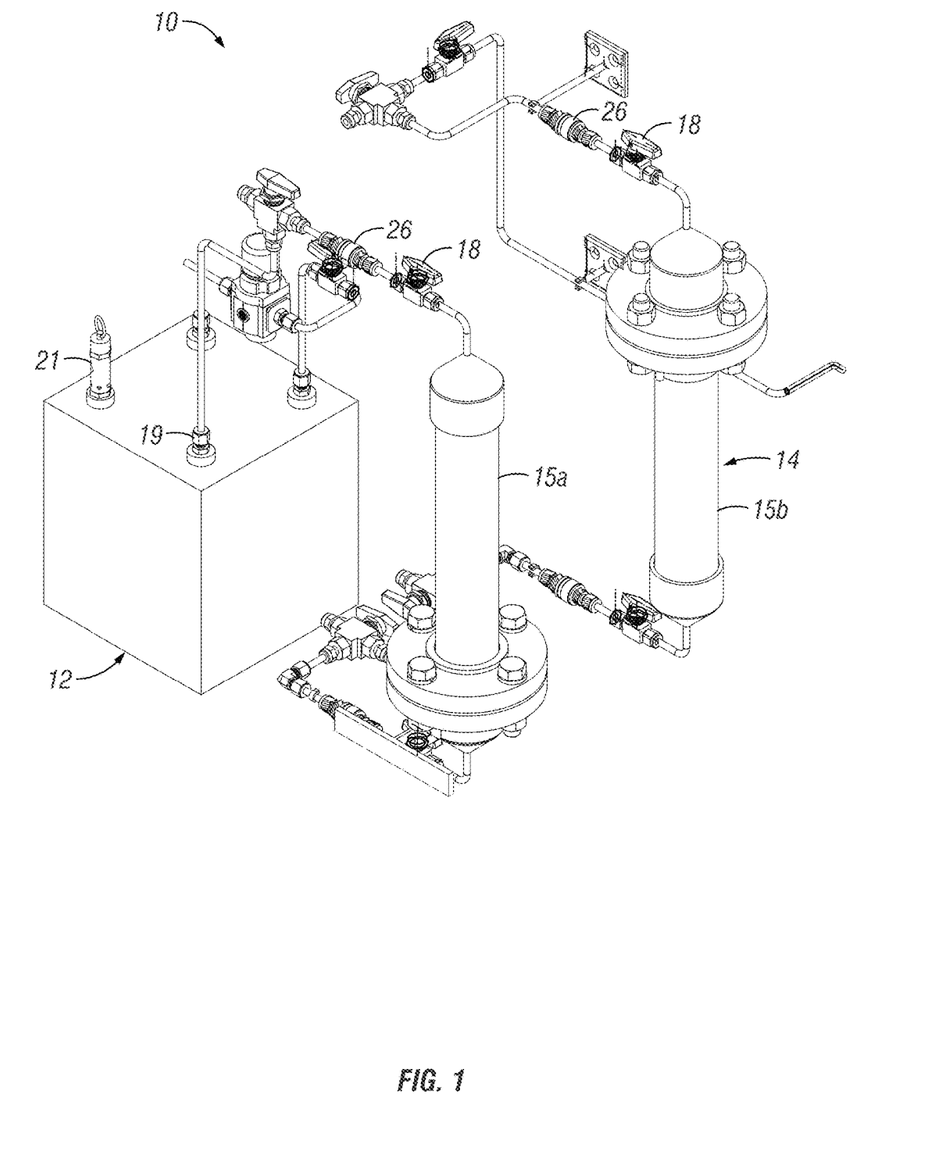
FIG. 1 is a depiction of a system used for the purification of monomers (styrene) according to aspects of the present disclosure.
Figure 2:
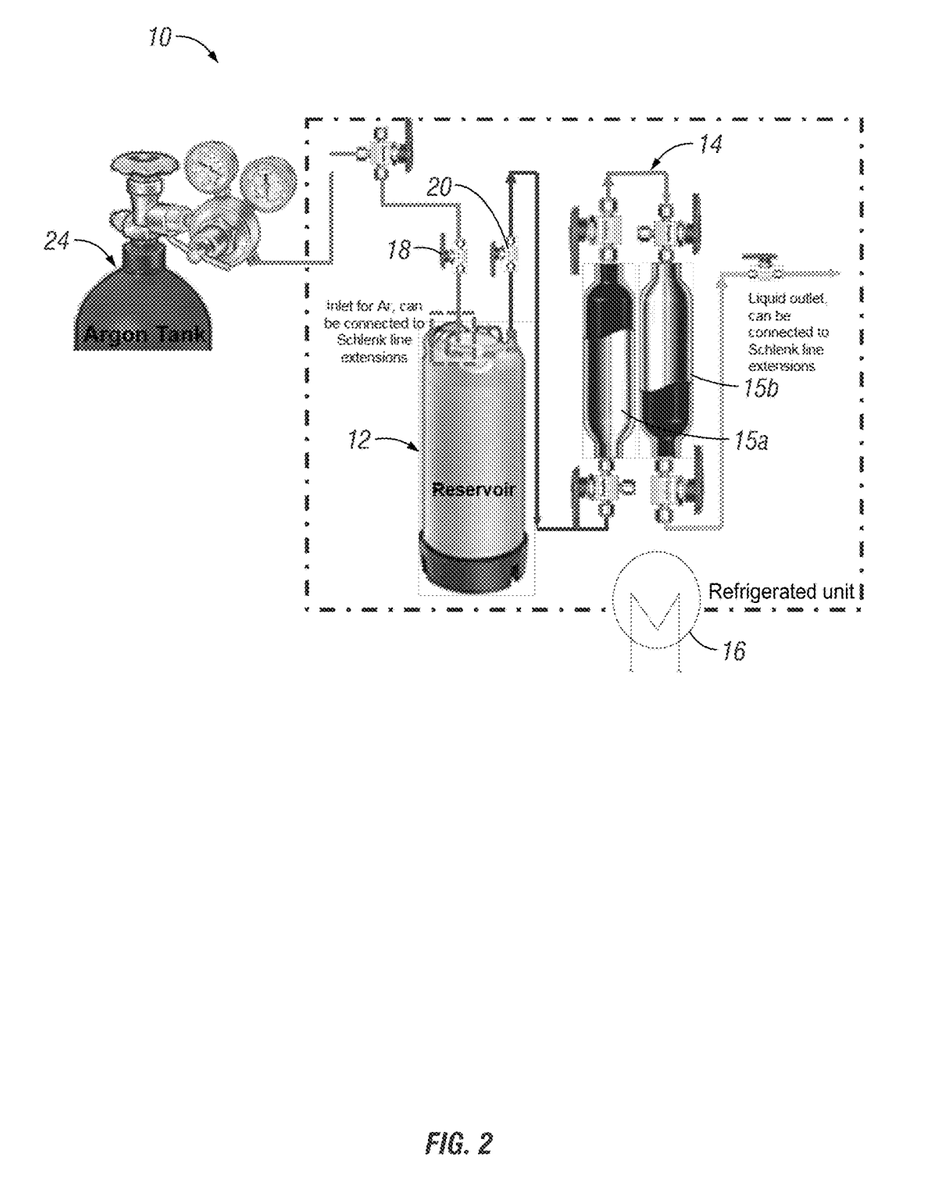
FIG. 2 is a diagram of a purification system according to aspects of the disclosure.

FIG. 1 shows a depiction of an exemplary purification system 10 according to aspects of the disclosure that is used to purify monomers, such as styrene. Accordingly, the purification system 10 comprises an enclosed system containing a reservoir tank 12, one or more activated alumina columns/column systems 14 or other types of cleaning agents, as will be disclosed, and a series of valves connected through high pressure rated stainless steel tubing. An exemplary set up of a purification system 10 is shown in FIG. 2. The system 10 facilitates purging, collecting and storing the purified contents air and moisture free. Moreover, this system 10 can be easily carried around on a small cart that can be on wheels or other means for easy movement of the system and can be stored in chemical storage freezers.

An aspect of the purification system 10 of the present disclosure provides that the system is refrigerated during operation. The refrigeration of the system prevents or otherwise mitigates the reaction of the reagents (e.g., monomers) being purified by the components disclosed herein. The columns and cleaning agents 14 associated therewith will remove inhibitors associated with the reagents and the refrigeration will mitigate these inhibitor-free materials from reacting. As will be understood, a refrigerant tank or other source 16 can be operatively connected to the system 10 to provide for the refrigeration of the system, which allows for the purification of the reactive chemicals without the volatile inputs of conventional purifying system. The purification system 10 could be refrigerated in a number of ways. Furthermore, the unit could be built into a small refrigerated unit which will be on wheels for mobility.

Many monomers and/or other reactive chemicals are shipped from suppliers loaded with good amount of inhibitors. These inhibitors would prolong the life of the material by preventing side reactions and auto-polymerization side effects. According to aspects of the present disclosure, the packed columns 14 may have some uninhibited monomer susceptible to side reactions and cause damage to packing in the column (most of the cases the column should just be replaced with a new one). Tests of the purification system of the present disclosure have been successful in keeping the column safe from side reactions and also store the monomer in the reservoir in safe conditions by storing the whole system in a refrigerator.

As shown in FIG. 2, the reservoir tank 12 contains an amount of a monomer to be purified by the system 10. The reservoir 12 can be generally any holding device for holding an amount of material (i.e., monomer) that is to be purified via the system. The reservoir tank 12 shown in the figure can hold approximately 1-2-gallons. It is a stainless steel tank equipped with inlet and outlet (with gas sparger) valves 19, 20, a pressure relief valve 21, and a handle to facilitate input of the monomer to be cleaned, inert gas purging, output of the monomer to columns, and maintain air-tight environment for extended periods of time. There may also be one or more additional valves that can be used, in part, for refilling the reservoir 12. Any tank 12 with capabilities can be utilized as part of the present disclosure. An inert gas 24, such as argon as shown in the figure, is operatively connected to the reservoir 12. For example, steel tubing can be used to connect the inert gas 24 and the reservoir 12, with one or more valves positioned therebetween to control the flow/pressure of the inert gas. A pumping mechanism, such as any type of pump, can be included to aid in controlling the flow of the inert gas into and/or through the system. The connection between the gas source 24 and the purification unit 10 can be via quick connects to allow for quick and easy hookup of the system to perform the purification process. However, it should be appreciated that other types of connectors used with gases and/or liquids could be used as part of the present disclosure. Furthermore, it is contemplated that the quick connects be utilized with the columns to be able to swap out columns as needed. For example, the columns will have a life span and after which, they will need to be refurbished or otherwise replaced. Utilizing the quick connect couplings would allow the columns to be quickly removed and replaced without much downtime.

Figure 3:
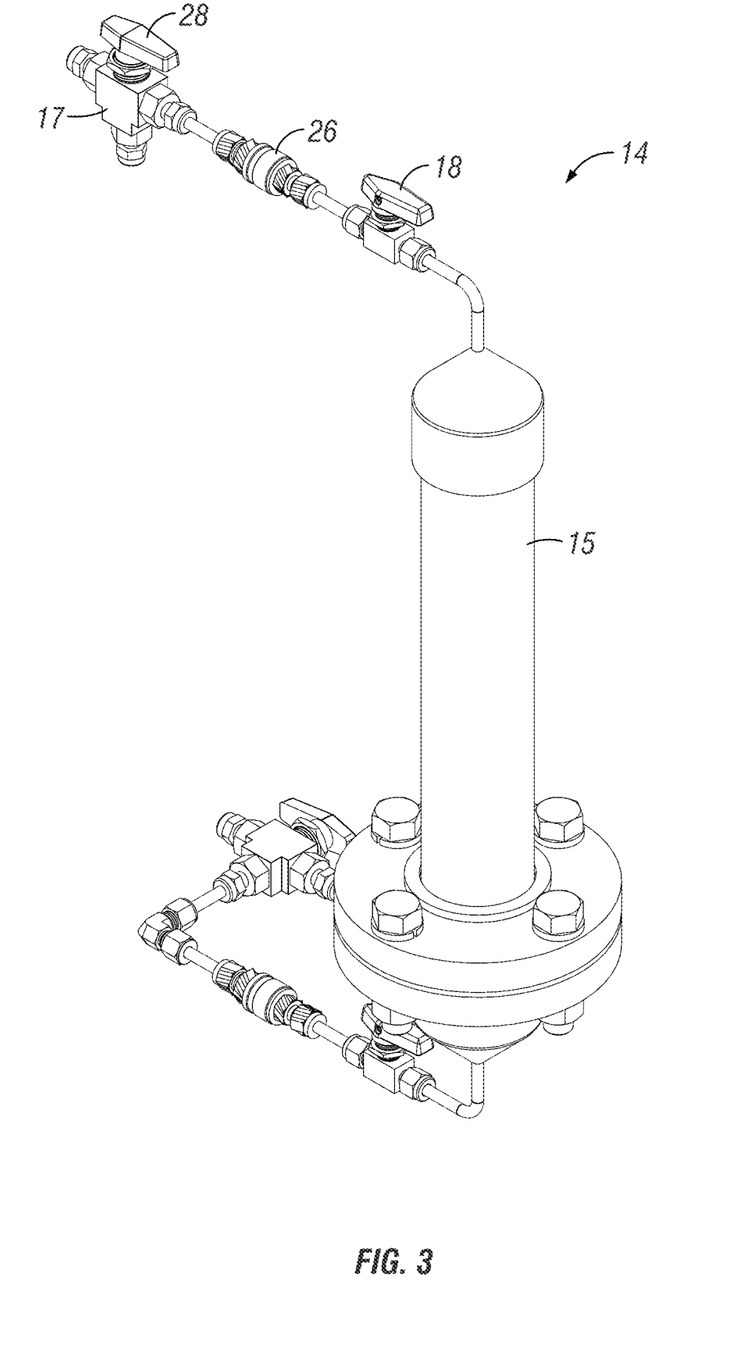
FIG. 3 is an isometric view of a column system for use with the purification system according to aspects of the disclosure.
Figure 4:
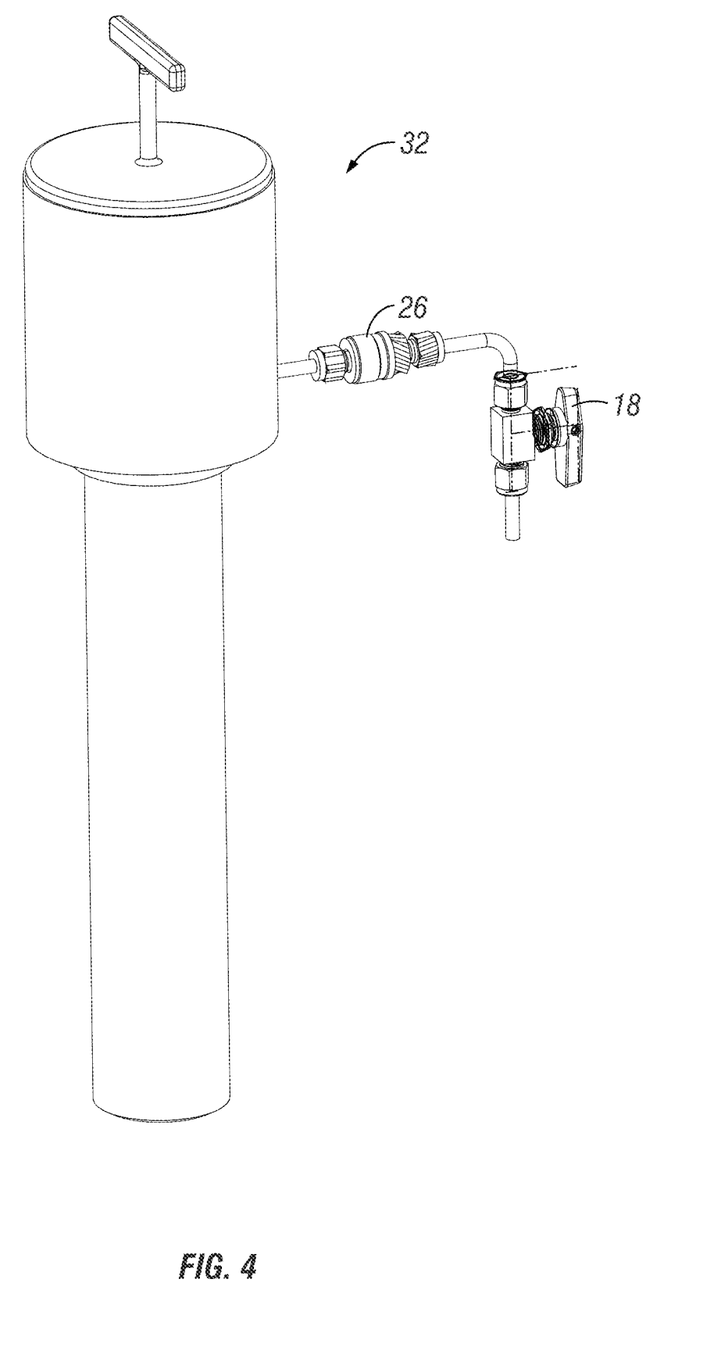
FIG. 4 is an isometric view of a reservoir refilling system according to aspects of the disclosure.

For example, FIG. 3 shows an isometric view of a column system 14 according to aspects of the disclosure. As shown in FIG. 3, the columns 15 holding the adsorbent material can be replenished/replaced after they are spent (meaning the adsorbent material gets exhausted and needs to be replaced with new adsorbent material). To ease the column replacement process for the user, reduce the time needed to replace the columns 15, and minimize the exposure of the system to outside atmosphere (system should always be maintained inert), the disclosure includes a method of column replacement. Columns 15 containing the adsorbent material are connected to the system 10 using a sequence of valves 18 and quick connects 26. Spent columns can be removed from the system by operating the quick connects 26. Presence of quick connects 26 makes it easy to remove the columns 15 from the system 14. Once the spent columns 15 are removed, the purification system is shut-off up to the point 17 because of the presence of three-way valve 28 as shown in the Figure. New columns will be sealed by pressurizing the columns with inert gas. The user connects the new columns to the system via the quick connects 26, opens the three-way valve 28 to exhaust and opens the two-way valve 30 on the new columns. The pressurized inert gas will purge the exposed lines. Once the purge is completed, the valves will be directed in a way to guide the chemical flow into the columns and the system is ready to be used again.

The columns 15 comprise a stainless steel tube with two caps positioned at each end. For example, the caps can be welded or screwed at each end, or can otherwise be positioned. The columns 15 for use with the disclosure as presently disclosed can be fabricated on an as-needed basis, or can purchased already made and generally ready-to-use.

Returning to FIGS. 1-3, it is contemplated that the columns used in the disclosure could incorporate different cleaning agents, as will be understood. Particular cleaning agents/column combinations could be better used to purify particular reagent/inhibitor combinations. Therefore, according to some aspects of the disclosure, the columns could be swapped out via the quick connects to pair the desired cleaning agent with the reagent that is being purified with the system disclosed herein.

However, it should also be appreciated that the quick connects not be utilized in all embodiments, and traditional connection methods (clamps, nut and bolts, etc.) could also be utilized with the system disclosed.

The inert gas is used to push the chemical stored in the reservoir through the purification system. The use of an inert gas ensures that the interaction between the inert gas and the chemical to be purified will not interact to contaminate the chemical. As inert gases are non-reactive, they are ideal to be used to aid in moving the purifying chemical through the system.

The valves of the system are generally one-way valves that prevent the backflow of the inert gas, the chemical to be purified, and/or any combination of the same from flowing backwards through the system. The number of valves used can be determinative upon many factors, including, but not limited to, the size of the system, the amount of product (chemical) to be purified, the required pressure to move through the system, the inert gas used, the type of chemical to be purified, the temperature of the system, among others. For example, it may be desired to maintain a pressure in the system during the purification process. Having more valves allows for smaller segments of pipes to be pressurized, which reduces the pressure burden of the system. This also provides a failsafe, should one or more of the valves fail. The valves may be check valves, butterfly valves, ball valves, diaphragm valves, solenoids, angle valves, or any combination of the same. It should be noted that the system can become automated with the use of solenoids connected to an intelligent control, such as a central processing unit (CPU), server, or other computing device. A user interface could also be connected to the intelligent control to aid in the automation process.

It should also be appreciated that the system could include, at either or both of the inlet and the outlet ports to attach to a Schlenk line or other vacuum gas manifolds.

Also shown in FIGS. 1-3 are first and second activated alumina columns 14a, 14b. While two of the columns are shown in the figure, it should be appreciated that this is not a requirement for the disclosure, and instead, the setup is shown for exemplary purposes. As will be appreciated, the number of columns may be determined based upon the particular use/need of the purification system, and can include generally any number of columns to complete the purification process.

As disclosed, the columns can comprise activated alumina. Activated alumina is manufactured from aluminum hydroxide by dehydroxylating it in a way that produces a highly porous material; this material can have a surface area significantly over 200 m$^2$/g. The compound is used as a desiccant (to keep things dry by absorbing water from the air) and as a filter of fluoride, arsenic and selenium in drinking water.

While alumina columns are shown in the figures, it should be appreciated that other types of cleaning agents could be used in place thereof. For example, it is contemplated that oxygen scavengers (Q5 catalyst), silica sand, molecular sieves, silica gel, etc., could be used in place of or in conjunction with the alumina columns. Still further, it is to be appreciated that other types of "cleaning agents" that are able to purify monomers, reactants, and/or other chemicals could be used and should be considered as part of the disclosure.

Still further, the disclosure provides for methods, apparatus, and/or systems for refilling the reservoir 12 of the purification system 10. As shown in FIG. 1, the reservoir tank 12 connected to the columns 14a, 14b holds the chemical to be purified. When the level of reservoir tank 12 reaches approximately 10% of the total volume, a new batch of chemical can be added using a siphon pump mechanism 32. To enhance the safety of the system, the tank 12 has been designed as a completely enclosed system with no lids. Because of this, new batch of chemical should be input to the system via use of a hand operated siphon pump 32. The pump 32 has attachments that can be secured directly to the chemical bottle and can input a gallon of chemical in as little as 3-minutes.

Figure 5A:
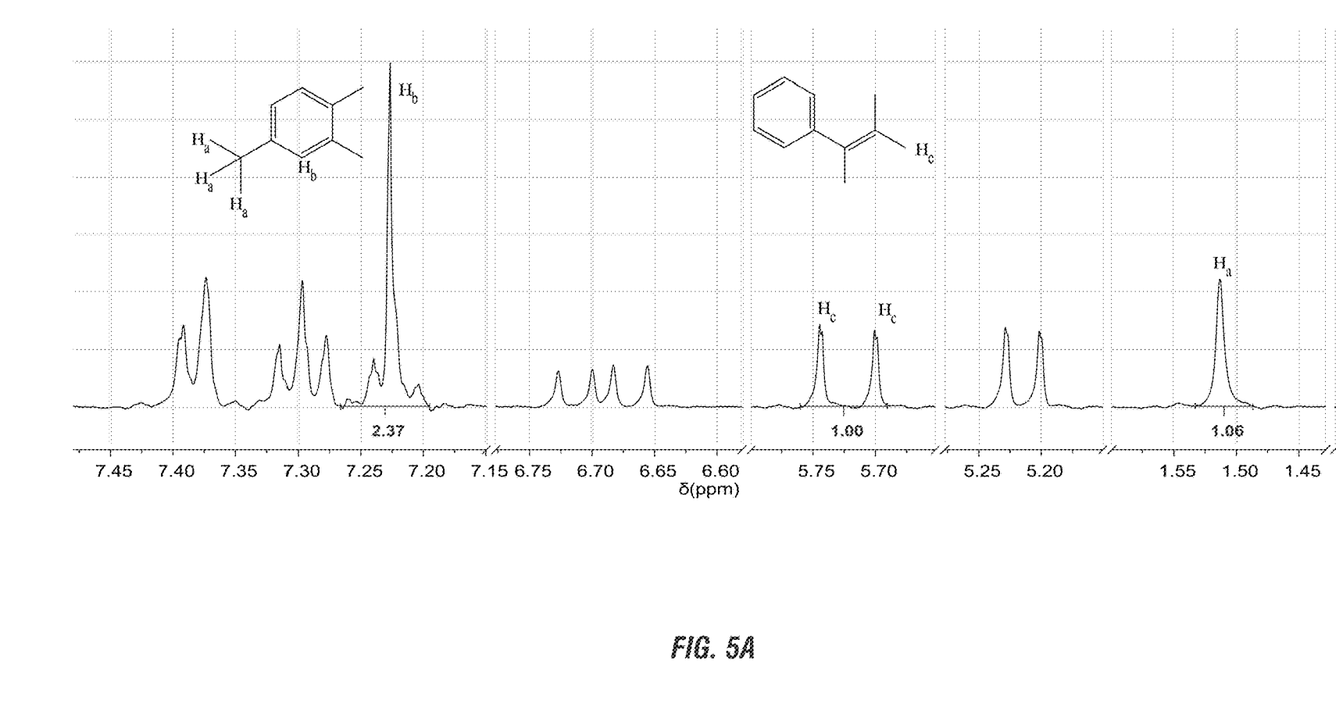
FIGS. 5A and 5B are graphs showing 1-Hydrogen Nuclear Magnetic Resonance of styrene monomer before and after passage through a purification system according to aspects of the present disclosure.
Figure 5B:
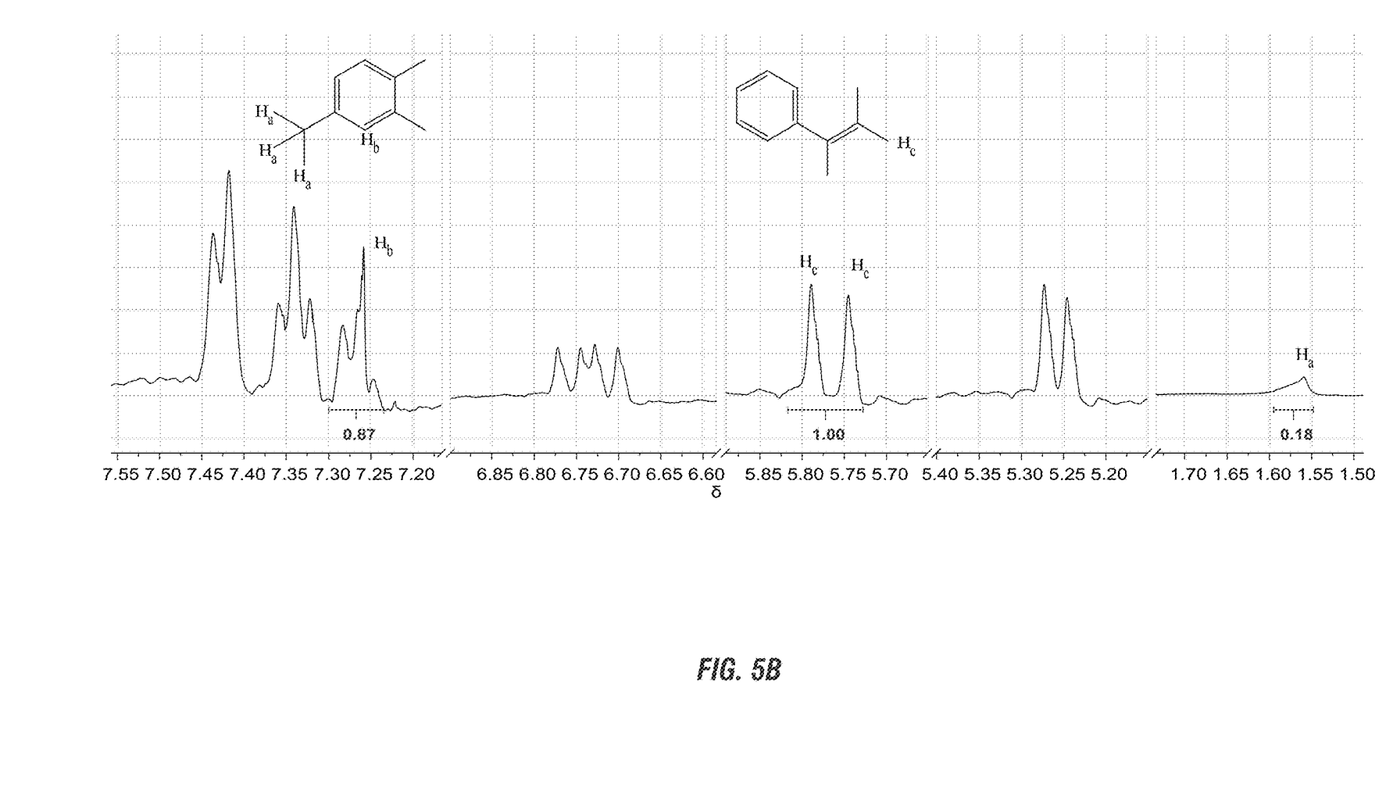
Figure 6:
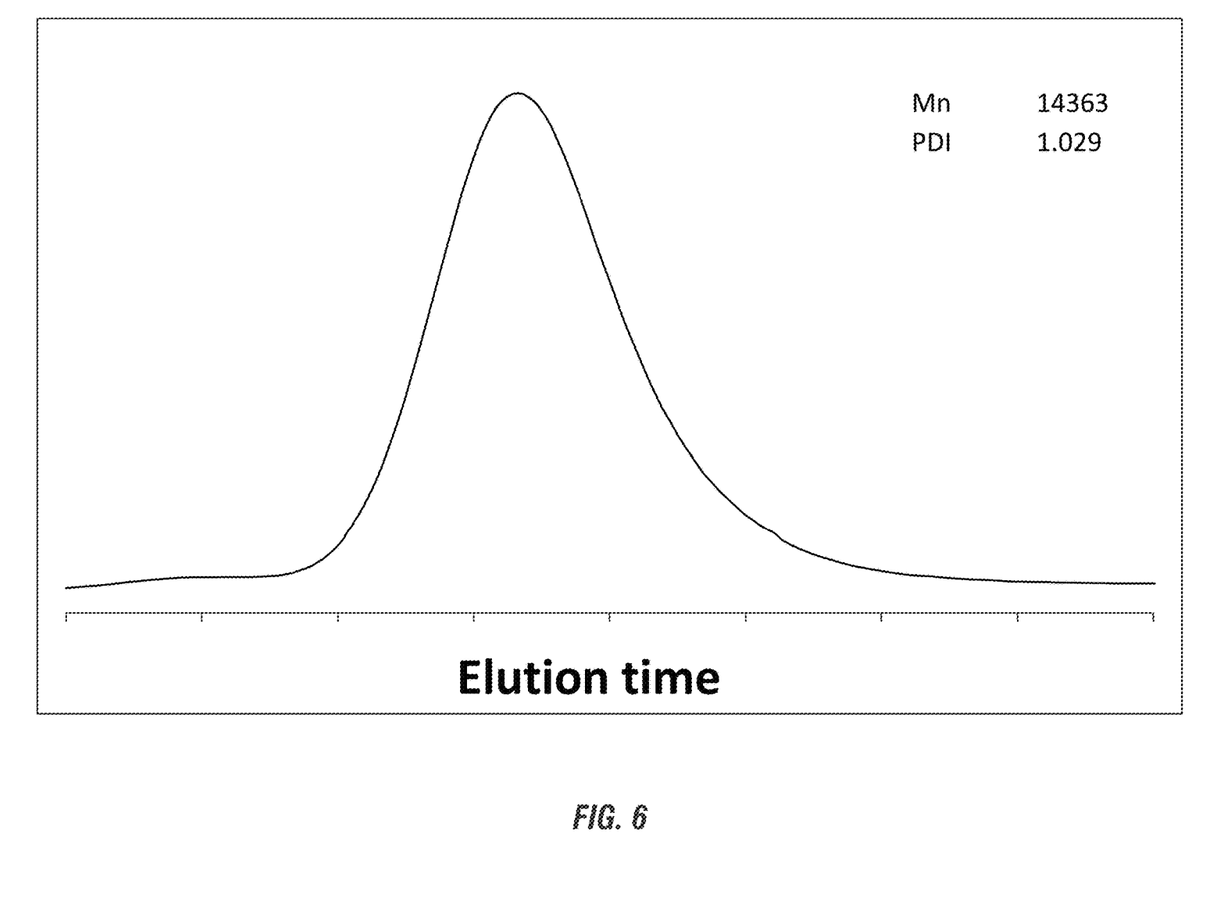
FIG. 6 is a graph showing Size Exclusion Chromatography of polystyrene synthetized via anionic polymerization from styrene purified through the purification system, methods, and apparatus of the present disclosure.

Initial tests on the purity of the monomer were done using hydrogen nuclear magnetic resonance ($^1$H-NMR), see FIGS. 5A and 5B, where the bottom spectra shows the reduction in intensity of the inhibitor at around 1.5 and 7.2 ppm. FIG. 5A includes 1H-NMR showing styrene ($H_c$) and 4-tert-butylcatechol (BHT, stabilizer) ($H_a$ and $H_b$) before passing through the purification unit. All unlabeled peaks correspond to styrene. FIG. 5B includes 1H-NMR showing styrene (Hc) and 4-tert-butylcatechol (BHT, stabilizer) (Ha and Hb) after passing through the purification unit. All unlabeled peaks correspond to styrene. Size exclusion chromatography (SEC), see FIG. 6, was done after polymerizing the purified monomer using anionic polymerization showing a single narrow peak (low polydispersity, no secondary shoulders) with targeted molecular weight achieved.

EXAMPLE

A purification system was assembled and used for testing. The testing was for the purification of monomers. Table 1 lists dates the monomer purification system was used to dispense monomer, styrene, used for anionic polymerizations; and it also lists the targeted and obtained molecular weight of the polymers. These numbers show that the system, after 21 months, still is capable of purifying the monomer for anionic polymerization purposes.

TABLE 1

List of different polystyrene anionic polymerization reactions with the target and the obtained molecular weights are listed.

| Date | Poly(Styrene) Target Molecular Weight, [Da] | Poly(Styrene) Obtained Molecular Weight, [Da] |
| --- | --- | --- |
| June 2014 | 15,000 | 15,000 |
| July 2014 | 13,900 | 14,900 |
| July 2014 | 14,000 | 17,000 |
| September 2014 | 12,700 | 12,700 |
| September 2014 | 13,500 | 16,000 |
| December 2014 | 54,000 | 50,000 |
| March 2015 | 15,000 | 15,500 |
| April 2015 | 15,000 | 16,000 |
| February 2016 | 2,000 | 2,000 |
| March 2016 | 2,000 | 2,200 |

Therefore, the system as shown and described provides for the purification of a chemical, such as a monomer, that improves on or provides advantages over that previously known. In addition, the system of the present disclosure also greatly reduces the amount of time for the process. It has been shown that the purification process using aspects of the present disclosure can be completed in 0.5-1 hour, while conventional methods have taken 8-10 hours.

The compactness of the system provides additional advantages. This would allow the system to be standalone and portable, such that it can be easily implemented into a lab, while taking up a fraction of the space when compared to traditional processes.

Additional aspects of the system include that the process could be adapted to use the process for a broad range of reactive chemicals, including monomers.

It should also be noted that, while the disclosure has included the example of styrene herein, it is to be appreciated that generally any type of reactive chemical and/or reactant could be purified via the disclosed. The disclosure should not be limited to the purification of certain types of chemicals and instead, should be considered for substantially any and all purification.

Therefore, a system, method, and/or apparatus for purifying monomers has been shown and described. It is to be appreciated that any number of changes be contemplated by the disclosure, and that the disclosure need not be limited to the exemplary aspects disclosed herein. That which has been described is merely exemplary. The present invention contemplates numerous variations, options, and alternatives fall within the spirit and scope of the invention.

What is claimed is:

1. A purification system for purifying reagents, comprising:
   a reservoir containing the reagent to be purified;

one or more columns embedded in a refrigeration system and including one or more cleaning agent in line with the reservoir, wherein the reagent is transferred from the reservoir and into and through the one or more columns with the one or more cleaning agent for purification of the reagent; and an outlet for dispensing of purified reagent after it has passed through the one or more columns;

wherein the one or more cleaning agent comprises:
  a. activated alumina (basic, neutral, acidic);
  b. oxygen scavengers (Q5 catalyst);
  c. silica sand;
  d. molecular sieves;
  e. silica gel; or
  f. Ion exchange resins.

2. The purification system of claim 1, further comprising:
an inert gas in contact with the reagent in the reservoir and used to drive the reagent through the columns and towards the outlet; and
a pumping mechanism to aid in movement of the reagent into and through the one or more columns.

3. The purification system of claim 2, wherein the inert gas, reservoir, and one or more columns are connected via tubes.

4. The purification system of claim 3, wherein the tubes comprise high pressure rated stainless steel tubing.

5. The purification system of claim 4, further comprising one or more backflow prevention mechanisms in line with the tubing.

6. The purification system of claim 5, wherein the backflow prevention mechanisms comprise one-way valves.

7. The purification system of claim 1, further comprising a portable cart for holding the reservoir, columns, and outlet, and wherein the portable cart includes wheels for moving the system.

8. The purification system of claim 1, wherein the one or more cleaning agent comprises a combination of (a)-(f).

9. The purification system of claim 1, wherein the refrigeration system comprises a refrigerator.

10. A purification system for purifying agents, comprising:
a reservoir containing the reagent to be purified;
one or more columns positioned in a refrigeration system and including one or more cleaning agent in line with the reservoir, wherein the reagent is transferred from the reservoir and into and through the one or more columns with the one or more cleaning agent for purification of the reagent;
tubing operatively connected between the reservoir and the one or more columns for passing the reagent; and
one or more quick connect valves in line with the tubing to allow the one or more columns to be quickly and easily connected, via the tubing, to the reservoir for use, repair, or replacement;
wherein the one or more cleaning agent comprises:
  a. activated alumina (basic, neutral, acidic);
  b. oxygen scavengers (Q5 catalyst);
  c. silica sand;
  d. molecular sieves;
  e. silica gel; or
  f. Ion exchange resins.

11. The purification system of claim 10, further comprising one or more valves in line with the tubing to selectively allow the passage of the reagent through the tubing.

12. The purification system of claim 11, further comprising an outlet for dispensing of purified reagent after it has passed through the one or more columns.

13. The purification system of claim 10, wherein the refrigeration system comprises a refrigerator.

14. The purification system of claim 10, wherein the tubing comprises high pressure rated stainless steel tubing.

15. The purification system of claim 10, further comprising a pump operatively connected to the reservoir for refilling the reagent of the reservoir.

16. The purification system of claim 15, wherein the pump comprises a hand operated siphon pump.

* * * * *